United States Patent [19]
Genovese et al.

[11] Patent Number: 5,811,059
[45] Date of Patent: Sep. 22, 1998

[54] AUTOMATED, ON-DEMAND ION MOBILITY SPECTROMETRY ANALYSIS OF GAS CHROMATOGRAPH EFFLUENTS

[75] Inventors: James A. Genovese, Street; Charles S. Harden; A. Peter Snyder, both of Bel Air, all of Md.

[73] Assignee: The United States of America as represented by the Secretary of the Army, Washington, D.C.

[21] Appl. No.: 544,241

[22] Filed: Oct. 16, 1995

[51] Int. Cl.$^6$ ................................................. G01N 30/02
[52] U.S. Cl. .......................... 422/89; 73/23.42; 96/102; 250/287; 250/288; 422/98; 436/153; 436/161; 436/173
[58] Field of Search ................................ 436/161, 173, 436/153; 422/70, 89, 98; 73/23.37, 23.4, 23.42; 95/82; 96/101, 102, 103, 106; 250/287, 288

[56] References Cited

U.S. PATENT DOCUMENTS

| | | | |
|---|---|---|---|
| 4,970,905 | 11/1990 | McClennen et al. | 73/864.34 |
| 5,196,039 | 3/1993 | Phillips et al. | 210/656 |
| 5,376,277 | 12/1994 | Cortes et al. | 210/659 |
| 5,457,316 | 10/1995 | Cohen et al. | 250/286 |

OTHER PUBLICATIONS

Mievre, Anal. Chem., vol. 45 No. 11, pp. 1981–1983 (1973).

*Primary Examiner*—Jan Ludlow
*Attorney, Agent, or Firm*—Edward L. Stolarun; Ulysses John Biffoni

[57] ABSTRACT

A chemical sampling apparatus including an interface between a miniature ion mobility spectrometer and a gas chromatography system. The apparatus has a gas chromatography an ion mobility spectrometer and an input for inputting a regulated flow of a gas to be analyzed to the gas chromatograph. An interface is positioned between the gas chromatograph and the ion mobility spectrometer. The interface accepts and analyzes eluted gas from the gas chromatograph and selectively inputs the eluted gas to the ion mobility spectrometer only when an eluted gas condition to be analyzed is detected.

7 Claims, 6 Drawing Sheets

Miniature GC/IMS Sampling Mode

AUTOMATED, ON-DEMAND ION MOBILITY SPECTROMETRY ANALYSIS OF GAS CHROMATOGRAPH EFFLUENTS

BACKGROUND OF THE INVENTION

1. Field of the Invention

The present invention pertains to a chemical sampling apparatus or more particularly to an interface between a miniature ion mobility spectrometer and a gas chromatography system.

2. Description of the Prior Art

Miniature ion mobility spectrometers (mini-IMS) are known in the art. A typical mini-IMS is a 2×8×1 inch rectangular, self-contained device that detects chemical agents in atmospheric vapors by ion mobility spectrometry. Ion mobility spectrometry is a vapor detection technique that is performed at atmospheric pressure. A vapor or gaseous sample is admitted into an ion mobility spectrometer via a pumping system. The vapor is ionized and the ions are held in a region by certain voltage gates. The gate is pulsed in a negative or positive direction depending on whether positive or negative ions are to be detected. The ions drift or travel down an electrical tube that focuses the ions to a Faraday cup detector. Typical ion currents between the voltage gate and detector are in the picoampere range. Millisecond times characterize the times needed for the ions to drift to the detector and this occurs at atmospheric pressure. Therefore the mass, as well as the ionic cross section dictates the speed that the ions travel down the electrified drift tube. Conventional ion mobility spectrometers utilize considerable power in pumping sample into the system, providing for internal air flows and exhausting the air. Molecular sieve packs effect the cleaning and drying of the air. Conventional ion mobility spectrometry uses a continuous feed through of sample and air make-up gases in the neutral state. They are ionized and are repeatedly pulsed down the electrical drift tube to provide for detection events. The system has a polysilicone membrane between the atmosphere and drift tube, therefore, sample must pass through the membrane. Some compounds show tailing due to this semi-permeable barrier. In a mini-IMS, molecular sieves replace the pumps. The sieves provide for a clean, dry drift tube. A small loudspeaker is activated to displace its diaphragm and the amount of displacement dictates the defined, discreet volume of sample that enters a pinhole opening in the mini-IMS. No membrane is present. Sample is ionized and detected.

Gas chromatography (GC) is also very well known. However, it is used in a continuous fashion, i.e., either sample and/or makeup gas continually flows through the GC column. Sample can flow through a GC column by either a positive pressure at the entrance of the column or by reducing the pressure at the column outlet. The concept of combining or interfacing two separate, stand-alone instruments is also known in the art. An interface between two analytical instruments, i.e., a GC with mass spectrometer (MS) is described by "The Hyphenated Technique," Hirschfeld, Tomas, Analytical Chemistry, 52, p. 297A–312A (1980) wherein many combinations of various stand-alone instruments are proposed. In this prior method, a sample passes through and is processed by the first instrument, exits the first instrument, enters and is processed by the second instrument and is finally detected by the detector residing in the second instrument. GC columns connected to MS detectors is known to the skilled artisan. GC provides continuous analysis times from time 0 up, where time is measured in seconds, minutes or even hours. IMS also has a continuous analysis time frame, however, it is measured in milliseconds, typically from 4–14 msec. IMS spans masses from 1 atomic mass unit (amu) up to a million and beyond and fractional masses are allowed. Since this is a wide range, great selectivity can be obtained. However, the mini-IMS, with a 4–14 msec measuring span, has relatively low selectivity but has greater specificity for the compounds in question. Electromagnetic radiation spectrometers measure in wavelengths, from 200 nm to over 3000 nm. This spans the far UV to IR region. Thus, when two instruments are connected in tandem, a full three dimensional analysis of a sample can be done. For GC-IMS, this is characterized by a three axis graph which denotes GC retention time, IMS drift time, and signal intensity. These techniques, by necessity, dictate, that when the sample exits the first instrument, it automatically enters the second instrument. There are also GC instruments arranged such that part of the eluate goes to an MS detector and the other part of the sample enters a radiation spectrometer such as a Fourier Transform infra-red spectrometer. Here also, the sample eluting from the GC goes to both instruments. Conventional GC systems can also have a non-dimensional detector connected to themselves. These types of detectors are much less expensive than the one-dimensional detectors. Non-dimensional detectors all operate on a yes/no or on/off basis. Either there is or is not a signal at a given GC retention time, while for a one dimensional detector, the presence/absence of a sample is noted in a specific point in an entire dimension. This yields greater specificity than a simple yes/no indication.

Microchip gas chromatography systems are also known in the art. It is still further known in the art to provide a system by which atmospheric vapors are sampled and analyzed sequentially by a gas chromatograph and spectrometer. Such a system is disclosed in U.S. Pat. No. 4,970,905, which is incorporated herein by reference. The mini-IMS does not continuously interrogate sample, therefore, there can be times that a sample passes through the GC column and should not be pulsed or admitted into the mini-IMS. The operation of a combination GC-mini-IMS would be improved if an independent interface system monitored the GC effluent and prompted or slaved the mini-IMS at a specific time to take a sample. The present invention provides such an interface between a continuous flow microchip gas chromatography system and an intermittent sampling miniature ion mobility spectrometer. The invention provides an interface mechanism which independently and accurately directs the mini-IMS portion of the microchip GC/mini-IMS combination to "turn-on" and "turn-off" at specified times in order to optimally sample with the mini-IMS on demand and to obtain as many mini-IMS information data points as possible from an eluting sample peak from the end of a GC.

SUMMARY OF THE INVENTION

The invention provides gas analyzing apparatus which comprises a gas chromatograph, an ion mobility spectrometer and means for inputting a regulated flow of a gas to be analyzed to the gas chromatograph. An interface is positioned between the gas chromatograph and the ion mobility spectrometer. The interface is capable of accepting and analyzing eluted gas from the gas chromatograph and selectively inputting the eluted gas to the ion mobility spectrometer only when an eluted gas condition to be analyzed by the IMS is detected.

The invention also provides the above described interface as well as a method for analyzing a gas which comprises providing the above described apparatus and inputting a regulated flow of a gas to be analyzed to the gas chromatograph. The method provides causing the interface to accept and analyze eluted gas from the gas chromatograph and selectively inputting the eluted gas to the ion mobility spectrometer only when a condition to be analyzed is detected and then causing the miniature ion mobility spectrometer to analyze the gas input from the interface.

It is therefore an object of the invention to provide an improved chemical sampling apparatus. It is a further object of the invention to provide an interface between a miniature ion mobility spectrometer and a gas chromatography system.

DETAILED DESCRIPTION OF THE PREFERRED EMBODIMENT

Figure 1:
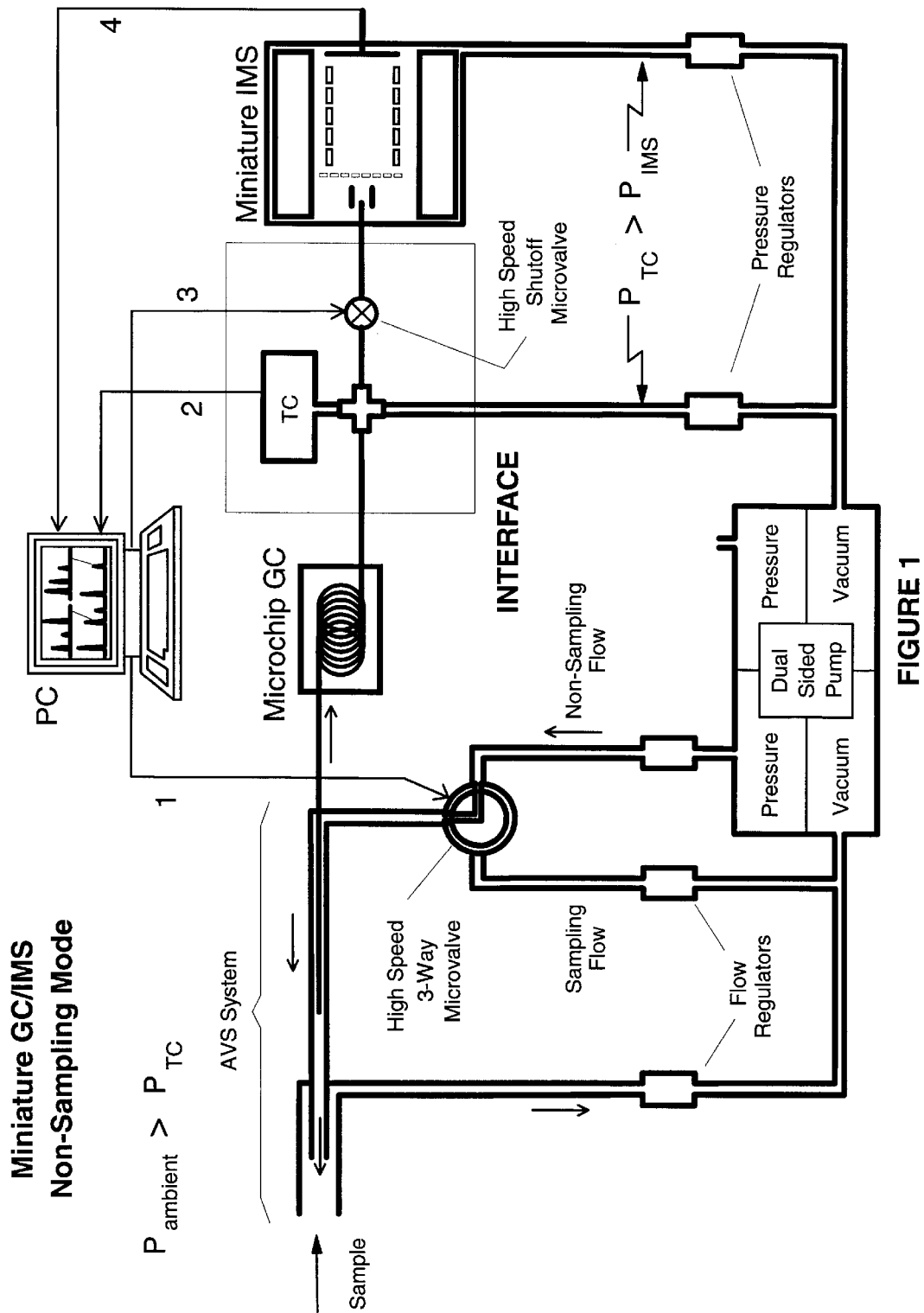
FIG. 1 shows a schematic representation of the apparatus of the invention operating in a negative pressure, non-sampling mode.

FIGS. 1–4 show a gas analyzing apparatus according to the invention, including a continuous flow, microchip gas chromatograph (GC), an intermittent sampling miniature ion mobility spectrometer (IMS) and an interface therebetween. The flow lines indicate sample flow direction and regulation by means of valves controlled by a computer.

The interface includes a non-dimensional detector such as a thermal conductivity detector (TC) or a one-dimensional detector which slaves the input of an instrumental detection device (mini-IMS here) to the output of a sample separation or delivery system (a GC here). The interface comprises a one dimensional or non-dimensional detector and a high speed shutoff valve which are computer controlled.

Non-dimensional detectors are much less expensive than the one-dimensional detectors. Examples include thermal conductivity (TC), refractive index, flame ionization, flame photometric, electron capture and Surface Acoustic Wave (SAW) detectors. For specific analyses such as those for phosphorus or sulfur compounds, the TC could be replaced by phosphorus or sulfur specific Flame Photometric Detectors (FPD). Electronegative analytes could be analyzed in this manner using Electron Capture detectors to trigger the mini-IMS. These detectors all operate on a yes/no or on/off basis. Either there is or is not a signal at a given GC retention time, while for a one dimensional detector, the presence or absence of a sample is noted in a specific point in an entire dimension. This yields greater specificity than a simple yes/no indication. One dimensional detectors include such as mass spectrometry or Fourier transform infrared spectrometry. The TC, which is preferred is a very small, approximately microchip size device and can operate at atmospheric pressure. The detector monitors the continuous effluent from the GC system and directs flow past, not into, the mini-IMS. When the TC detects a compound of interest, the TC causes the mini-IMS to take a sample at that time, thus, the mini-IMS can obtain a one dimensional information analysis with respect to the drift time of the sample in milliseconds. Directing the mini-IMS to sample at specified, discreet times optimizes the performance of the mini-IMS for both internal mini-IMS considerations, i.e., low contamination, less gas burden, and external mini-IMS considerations such as taking a sample at a time when it is already known, via the TC, that a sample is present.

Gas chromatographs useful for this invention are well known in the art and include microchip GC's and miniature GC's. Microchip GC's with a capillary gas chromatography column are commercially available in various inner diameters, lengths and inner coatings. A typical microchip GC is available through the Institute for Environmental Studies, Louisiana State University, Baton Rouge, La. Miniature ion mobility spectrometers (mini-IMS) are commercially available from Graseby-Ionics, Herts, UK. The GC is directly connected to the IMS ionization source, and the GC and IMS components operate independently of each other. The invention provides an interface mechanism to influence operation of the IMS portion as a slave detector to the GC section. Since the mini-IMS can sample on demand, this results in the IMS only turning on when a sample elutes or is emitted from the GC column. Thus it shuts itself off until directed to readmit a discrete amount of sample at a specified time.

Figure 2:
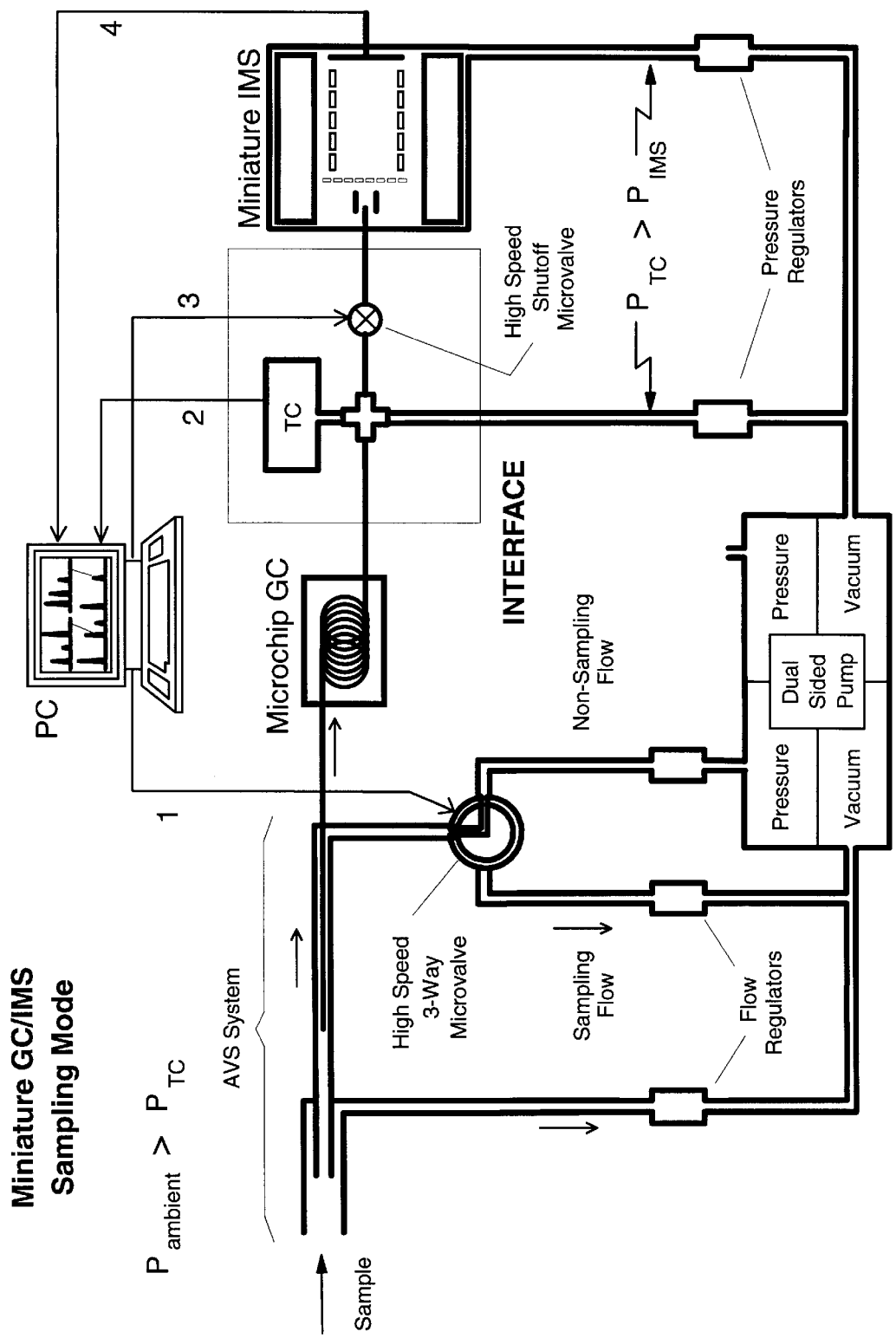
FIG. 2 shows a schematic representation of the apparatus of the invention operating in a negative pressure, sampling mode.

The apparatus can operate in two modes. One is where the sample flows through the GC/mini-IMS device by a negative pressure, i.e. pressure at GC entrance is ambient, pressure at the outlet of the GC is lower than ambient, and pressure in mini-IMS is lower than at the outlet of the GC. The other mode is by positive pressure, i.e., pressure at GC entrance is higher than ambient, pressure at outlet of GC is lower than at the GC entrance but higher than ambient, and the mini-IMS is at ambient pressure. In FIGS. 1–2, pressure at the IMS is less than ambient and in FIGS. 3–4, pressure at the IMS is at ambient. In these figures, dotted lines represent electrical connections. Solid lines represent air flow paths.

Figure 5:
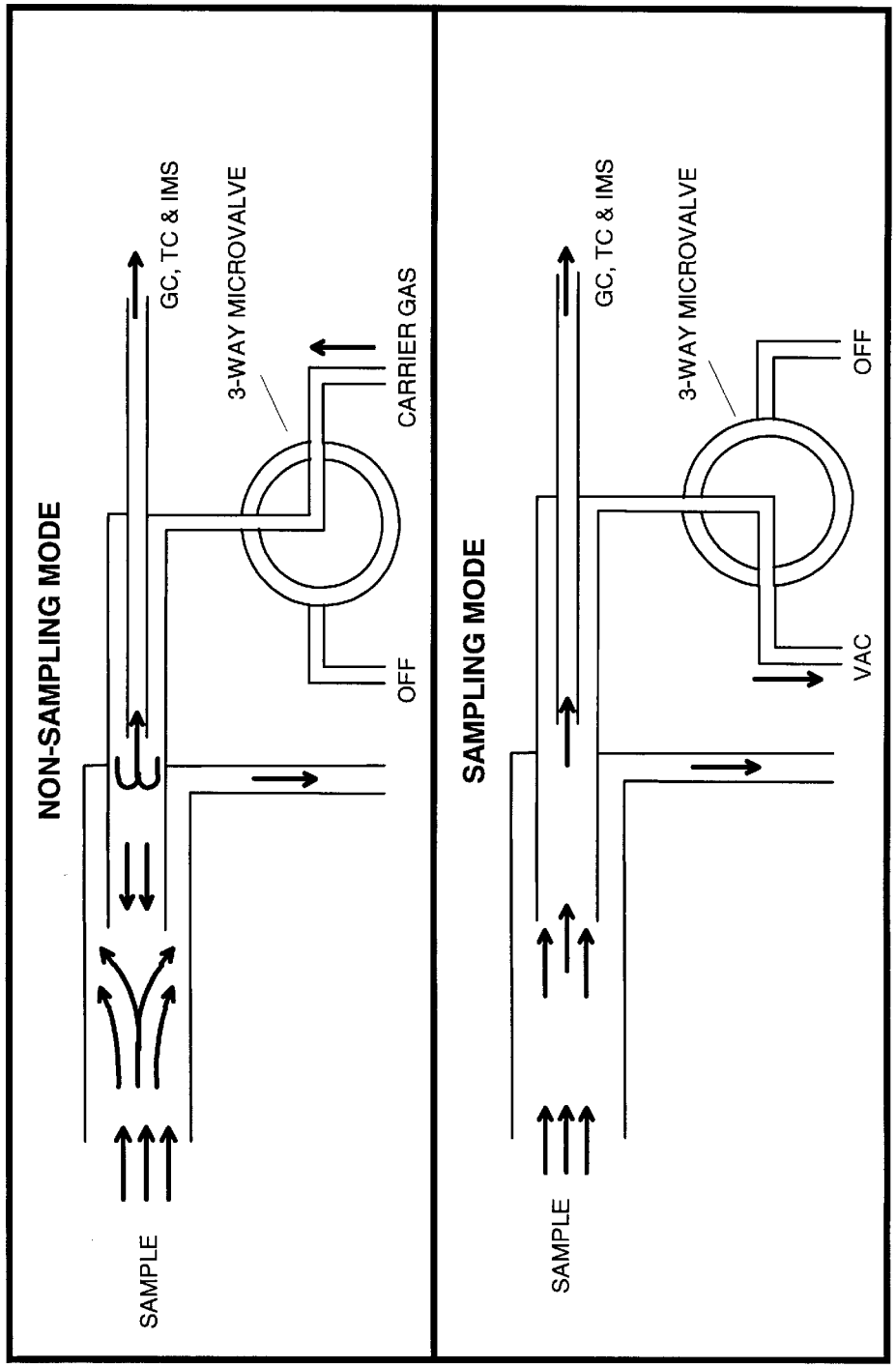
FIG. 5 shows a prior art automatic vapor sampler useful for the invention such as is described in U.S. Pat. No. 4,970,905.

A typical operation for a negative pressure condition is shown in FIGS. 1–2. FIG. 1 shows the non-sampling mode and FIG. 2 shows the sampling mode. The left side of the FIG. 1–2 apparatus comprises an automated vapor sampling inlet or AVS, according to U.S. Pat. No. 4,970,905, and which is detailed in FIG. 5. Since the GC is a continuous operation device, the AVS system must provide a continuous flow of clean air into the GC. An interface mates the AVS-microchip GC to a mini-IMS. In the preferred embodiment, the interface comprises a conventional thermal conductivity detector and a high speed shutoff microvalve. The high speed shutoff microvalve regulates the time and amount of sample air that enters the mini-IMS.

In the non-sampling mode of FIG. 1, clean ambient air having pressure greater than TC pressure, enters the left side of the apparatus via the left vacuum side of the dual sided pump. The flow regulators cause a non-sampling clean air flow to reach the GC and push away sample air. Clean air elutes from the TC, however when the TC detects only clean air it does not turn on the IMS and the clean air exhausts from the TC via the right side of the dual sided pump.

Figure 3:
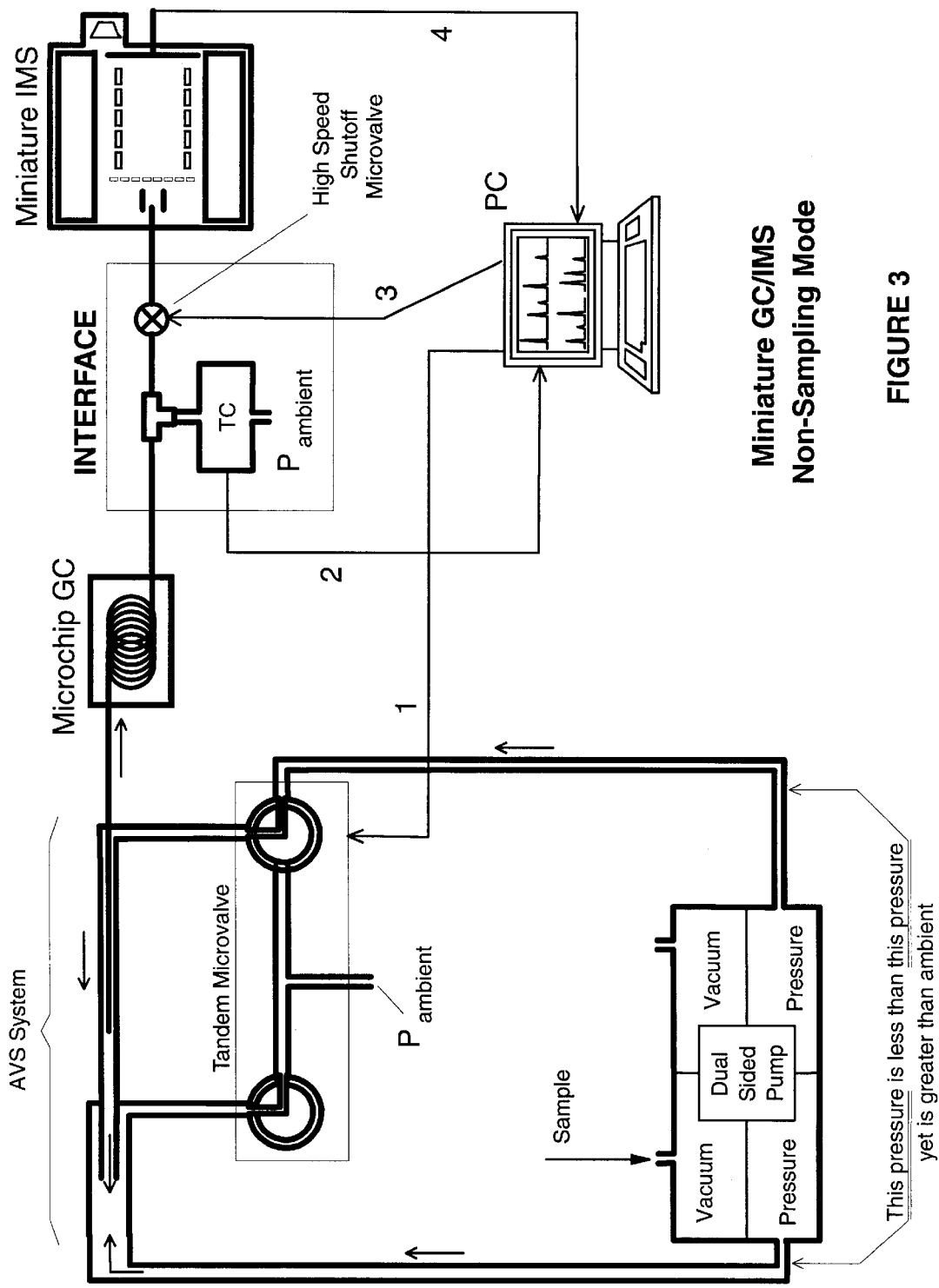
FIG. 3 shows a schematic representation of the apparatus of the invention operating in a positive pressure, non-sampling mode.
Figure 4:
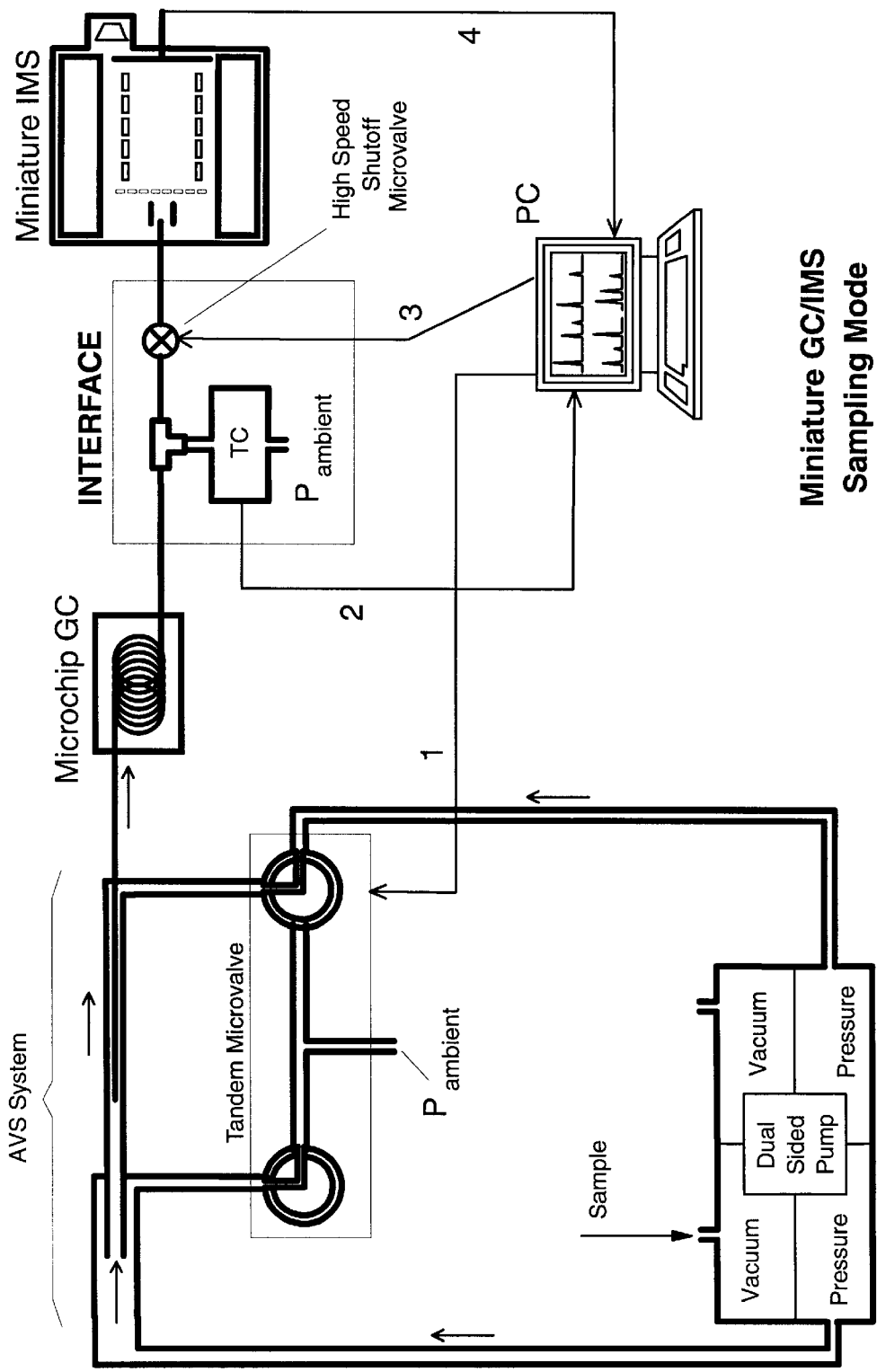
FIG. 4 shows a schematic representation of the apparatus of the invention operating in a positive pressure, sampling mode.

Referring to FIG. 2, a sample to be analyzed is admitted through the AVS. The AVS sample introduction system admits a discrete amount of vapor into the GC column via the high speed microvalve which is electrically controlled by a personal computer, PC or on-board chip. Dotted line 1 connects the personal computer to the AVS sample introduction system. The dual sided pump and flow regulators effect the flow of air and operates the AVS inlet. Separation of the compounds in the GC column occurs. Electrical line 2 connects the TC output to PC input. If no sample flows through the TC detector, then the mini-IMS is not activated. If the TC detects the presence of a substance, a signal is sent to the PC by path 2. This signal instructs the PC to first open the microswitch shutoff valve via path 3 and then to admit a small amount of sample, approximately 50 microliters, into the mini-IMS via the displacement i.e., the 50 microliter displacement volume, of a small radio loudspeaker that is internal to the mini-IMS. The TC signal can also be used for sample quantity measurement purposes. The TC signal is linear with sample concentration while the mini-IMS signal is non-linear with respect to sample concentration. Pathway 4 provides for data signals from the mini-IMS to the PC. The dual-sided pump provides for a continuous air flow from the AVS to the GC and through an exhaust. The TC allows the mini-IMS to act as a slave detector. The mini-IMS only admits discrete sample sizes for a specified time (0.1–2 seconds). The negative pressure sampling mode of FIGS. 1–2 requires a separate pump to effect a lower pressure inside the mini-IMS. The second type of operation is performed under positive pressure. The positive pressure mode is shown in FIGS. 3–4. FIG. 3 shows the non-sampling mode and FIG. 4 shows the sampling mode. The positive pressure system produces a flow of air through the system, as opposed to a vacuum in the mini-IMS in FIGS. 1–2. Sample is admitted into the GC column and is at a pressure greater than the ambient. Most of the sample is exhausted through the tandem microvalve as seen in FIG. 4. The sample goes through the GC and enters the TC device which is at atmospheric or ambient pressures. Sample analysis in the positive pressure mode is shown in FIG. 4. A sample is drawn into the GC via the AVS system. The sample travels through a tandem microvalve, i.e. two valves physically next to each other which both are activated by the same switch, to the GC, exits the GC, and enters the TC. When the TC senses that a compound is present, the TC sends a signal to the PC by line 2 and the PC opens the shutoff microvalve via line 3. At the same time, the PC activates the mini-IMS speaker diaphragm to produce a pulse. This pulse displaces approximately 50–100 microliters of air and this amount is admitted into the entrance of the mini-IMS when the shutoff microvalve is open. Then, the ion mobility signal that is detected at the Faraday plate detector is transmitted to the PC via line 4.

Figure 6:
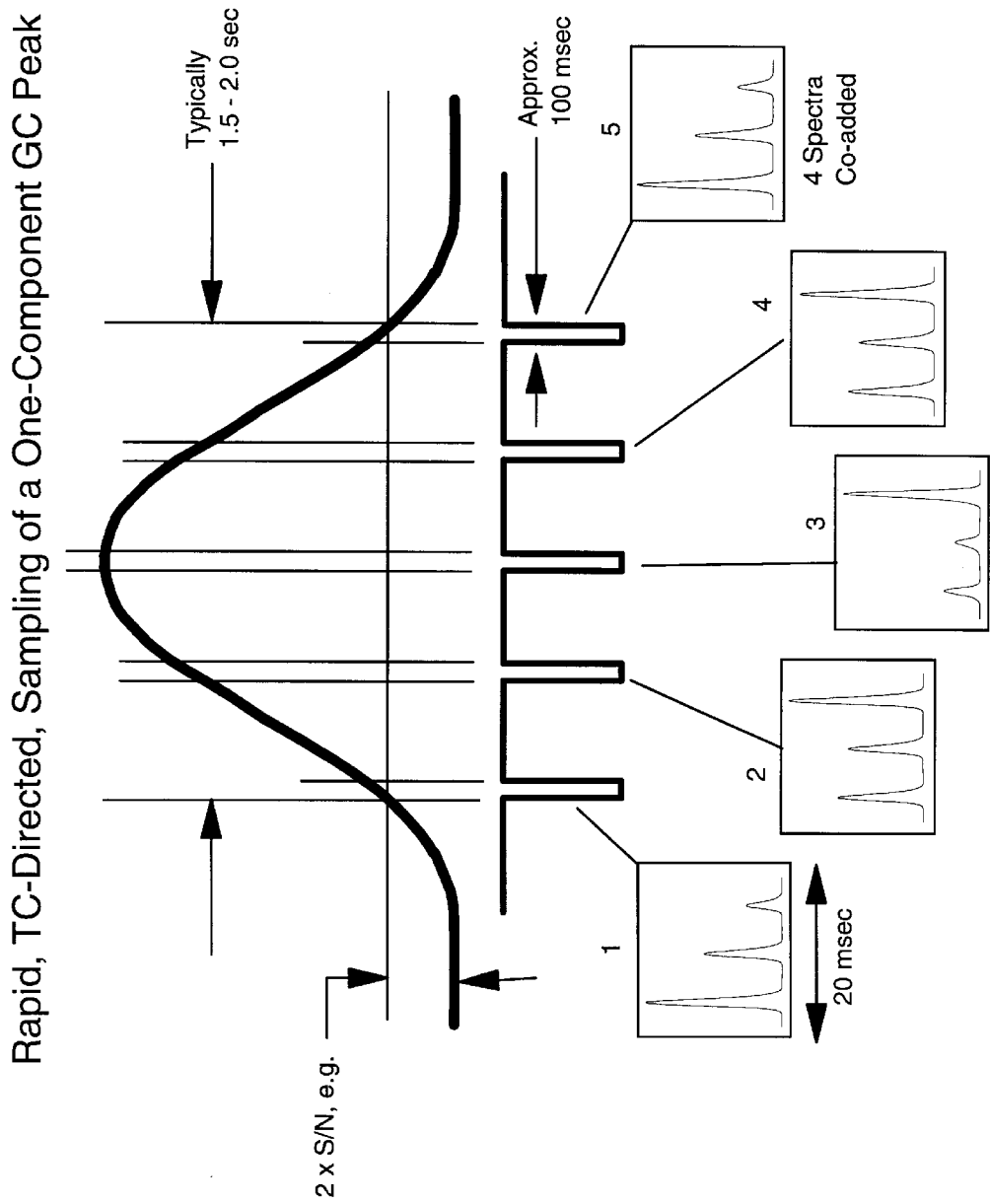
FIG. 6 shows a graphical analysis of GC peak response directed by the interface of the invention.

FIG. 6 demonstrates the benefit of the interface. The TC can direct the mini-IMS sampling of the GC peak during the GC elution of a compound. The steepness of the slope on both sides of the GC peak can be monitored by the TC. This can allow for the mini-IMS to sample more frequently during the presence of a compound. After the disappearance of the compound, then the mini-IMS would be dormant. Only the type of design concept as presented in the interface can cause this non-linear method of air sampling to occur. This non-linear method thus optimizes the performance of the mini-IMS and hence, the quality of data. The rate of sampling of a GC peak can be changed depending on the slope of the GC peak response. The rate can be uniform or non-uniform during the elution of a peak. When no sample is present, the TC will not direct a sampling event. FIG. 6 shows five different sampling events during a peak eluting, or five snapshots of the entire peak. The first sampling event occurs when the signal to noise ratio is 2:1 and each sampling event is 100 msec in durational. The second through fourth spectra in FIG. 6 show the typical changes that occur during the elution of a sample with respect to the first and fifth sample.

In the apparatus of this invention, the interface can take advantage of the sample on demand nature of the mini-IMS device and thus, the mini-IMS can act as a slave detector. The interface in the GC-IMS design provides for a better operation by increasing the probability of successful detection and identification of sample from the GC; minimizes the probability of mini-IMS signal overload and thus internal mini-IMS contamination and potential down-time and false signals.

While this invention has been described with reference to the within preferred embodiment and drawings, it is not to be limited thereby, and the invention is to be construed in accordance with the appended claims.

What is claimed is:

1. An apparatus for detecting the presence of and analyzing a component in a gas which comprises, (a) a gas chromatography;
 (b) an ion mobility spectrometer;
 (c) means for inputting a regulated flow of a gas to be analyzed to the gas chromatograph; and
 (d) an interface positioned between the gas chromatograph and the ion mobility spectrometer;
 (e) said interface including a detector for analyzing eluted gas from the gas chromatography, valve means directly connected to the ion mobility spectrometer for normally exhausting the analyzed eluted gas from said detector to preclude the analyzed eluted gas from entering the ion mobility spectrometer, and control means operatively connected to said detector and said valve means for selectively inputting a portion of the analyzed eluted gas to the ion mobility spectrometer for analysis in response to a detection signal from the detector corresponding to a component to be analyzed in the eluted gas.

2. The apparatus of claim 1 wherein the detection signal is the quantity by weight of a sample in the gas eluting from the gas chromatograph as determined by a gas chromatograph peak.

3. The apparatus of claim 1 wherein the detector comprises a one dimensional or non-dimensional detector.

4. The apparatus of claim 1 wherein the detector comprises one or more components selected from the group consisting of a thermal conductivity detector, surface acoustic wave detector, mass spectrometer, Fourier transform infrared spectrometer, flame photometric detector and an electron capture detector.

5. The apparatus of claim 1 wherein the control means comprises computer means and is operatively connected to the means for inputting.

6. The apparatus of claim 1 wherein the detector comprises a one dimensional or non-dimensional detector and the valve means comprises a shutoff valve.

7. The apparatus of claim 6 wherein the detector comprises one or more components selected from the group consisting of a thermal conductivity detector, surface acoustic wave detector, mass spectrometer, Fourier transform infrared spectrometer, flame photometric detector and an electron capture detector.

* * * * *